United States Patent [19]

Kühle et al.

[11] Patent Number: 4,474,808
[45] Date of Patent: Oct. 2, 1984

[54] PESTICIDALLY ACTIVE NOVEL N-SULPHENYLATED BIURET-N"-CARBOXYLIC ACID ESTERS

[75] Inventors: Engelbert Kühle, Bergisch Gladbach; Paul Reinecke, Leverkusen; Karl-Heinz Kuck, Langenfeld, all of Fed. Rep. of Germany

[73] Assignee: Bayer Aktiengesellschaft, Leverkusen, Fed. Rep. of Germany

[21] Appl. No.: 439,100

[22] Filed: Nov. 3, 1982

[30] Foreign Application Priority Data

Nov. 21, 1981 [DE] Fed. Rep. of Germany ....... 3146231

[51] Int. Cl.³ .................. A01N 47/34; C07C 149/437
[52] U.S. Cl. .............................. 424/300; 260/465 D; 424/285; 549/496; 560/10; 560/16; 560/115; 560/121; 560/125; 560/134; 560/136; 560/137; 560/148
[58] Field of Search ............... 560/148, 137, 134, 125, 560/121, 115, 16, 10, 136; 424/300, 285; 260/465 D; 549/496

[56] References Cited

U.S. PATENT DOCUMENTS 3,818,104  6/1974  Zielinski .............................. 424/285
4,369,189  1/1983  D'Silva .............................. 424/285
4,382,956  5/1983  Kühle et al. ........................ 424/285

FOREIGN PATENT DOCUMENTS 0010515  8/1980  European Pat. Off. .
2447626  4/1976  Fed. Rep. of Germany .
49-36706  10/1974  Japan ..................................... 560/16

OTHER PUBLICATIONS

*Synthesis*, 1982, No. 11, pp. 949–951, Kühle et al.

*Primary Examiner*—Natalie Trousof
*Assistant Examiner*—Patricia M. Scott
*Attorney, Agent, or Firm*—Sprung, Horn, Kramer & Woods

[57] ABSTRACT

N-Sulphenylated biuret-N"-carboxylic acid esters of the general formula

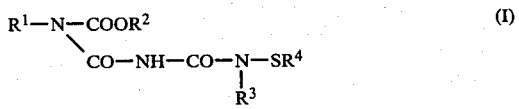

in which
R¹ and R² can be identical or different and represent an optionally substituted aliphatic, cycloaliphatic, aromatic or araliphatic radical,
R³ represents a hydrogen atom or an optionally substituted aliphatic, cycloaliphatic, araliphatic or aromatic radical and
R⁴ represents a trihalogenomethyl radical, are obtained by the reaction of an acyl isocyanate of the general formula

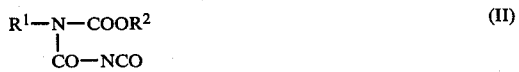

with a sulphenamide of the general formula

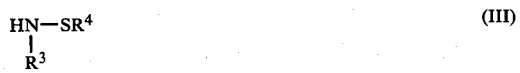

if appropriate in the presence of a diluent. The compounds of the formula (I) are new. They can be used as pest-combating agents which are microbicides, especially fungicides or bactericides.

10 Claims, No Drawings

PESTICIDALLY ACTIVE NOVEL N-SULPHENYLATED BIURET-N''-CARBOXYLIC ACID ESTERS

The present invention relates to certain new N-sulphenylated biuret-N''-carboxylic acid esters, to a process for their production, and to their use as pest-combating agents which are microbicides, especially as fungicides and bactericides.

Heavy metal salts of ethylene-1,2-bis-dithiocarbamic acid have long been in use in agriculture and horticulture for combating phytopathogenic fungi (R. Wegler, Chemie der Pflanzenschutz- und Schädlingsbekämpfungsmittel (Chemistry of plant protection agents and pest-combating agents), volume 2, page 65 Springer Verlag Berlin, Heidelberg, New York 1970).

Furthermore, it has been known for a long time that compounds containing N-trihalogenomethylthio groups can be used as fungicides in agriculture and horticulture. Thus, for example, N-(trichloromethylthio)-tetrahydrophthalimide (German Patent Specification 887,506) and N,N-dimethyl-N'-phenyl-N'-(fluorodichloromethylthio)sulphamide are employed in practice in fruit cultivation and viticulture for combating fungal diseases (Angew. Chem. 76, 807 (1964)).

Furthermore, it is known that 2-[(2,3-dichlorophenyl)-aminocarbonyl]-3,4,5,6-tetrachlorobenzoic acid (British Patent Specification 1,355,849) can be employed as a rice bactericide.

However, the action of the compounds mentioned is not always completely satisfactory, in particular when low amounts and concentrations are used.

The present invention now provides, as new compounds, N-sulphenylated biuret-N''-carboxylic acid esters of the general formula

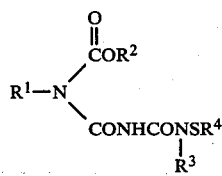
(I)

in which
R$^1$ and R$^2$ can be identical or different and represent an optionally substituted aliphatic, cycloaliphatic, aromatic or araliphatic radical,
R$^3$ represents a hydrogen atom or an optionally substituted aliphatic, cycloaliphatic, araliphatic or aromatic radical and
R$^4$ represents a trihalogenomethyl radical.

According to the present invention we further provide a process for the production of a compound of the present invention, characterized in that an acyl isocyanate of the general formula

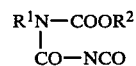
(II)

in which
R$^1$ and R$^2$ have the meanings given above,
is reacted with a sulphenamide of the general formula

(III)

in which
R$^3$ and R$^4$ have the meanings given above,
if appropriate in the presence of a diluent.

The new N-sulphenylated biuret-N''-carboxylic acid esters of the present invention possess powerful fungicidal and bactericidal properties. Some of them also exhibit an acaricidal action and an action against pests harmful to health and pests of stored products. Surprisingly, the compounds according to the present invention exhibit a substantially greater fungicidal action than the known compounds having the same direction of action, and the very good bactericidal action in rice should also be singled out, the compounds according to the invention having a superior action in this respect compared with the compounds known from the prior art. They thus represent an enrichment of the art.

Of the N-sulphenylated biuret-N''-carboxylic acid esters according to the invention, of the formula (I), those compounds are preferred in which
R$^1$ and R$^2$ are identical or different and represent an optionally substituted C$_1$ to C$_{10}$ alkyl, C$_2$ to C$_{10}$ alkenyl or C$_2$ to C$_{10}$ alkinyl radical, an optionally substituted C$_5$ to C$_{10}$ cycloalkyl radical or an optionally substituted aralkyl radical having 6 to 10 carbon atoms in the aryl part and 1 to 4 carbon atoms in the alkyl part, it being possible for the alkyl part to be straight-chain or branched, or represent a C$_6$ to C$_{10}$ aryl radical,
R$^3$ represents a hydrogen atom, an optionally substituted C$_1$ to C$_{10}$ alkyl, C$_2$ to C$_{10}$ alkenyl or C$_2$ to C$_{10}$ alkinyl radical, an optionally substituted C$_5$ to C$_{10}$ cycloalkyl radical, or an optionally substituted aralkyl radical having 6 to 10 carbon atoms the aryl part and 1 to 4 carbon atoms in the alkyl part, it being possible for the alkyl part to be straight-chain or branched, or represents an optionally substituted C$_6$ to C$_{10}$ aryl radical, and
R$^4$ represents a trihalogenomethyl radical.

Of the N-sulphenylated biuret-N''-carboxylic acid esters according to the invention, of the formula (I), those compounds are particularly preferred in which
R$^1$, R$^2$ and R$^3$ are identical or different and represent a C$_2$ to C$_{10}$, especially C$_3$ to C$_5$, alkenyl or C$_2$ to C$_{10}$, especially C$_3$ to C$_5$, alkinyl or C$_1$ to C$_{10}$, especially C$_1$ to C$_6$, alkyl radical which is optionally substituted by C$_1$ to C$_4$ alkoxy, C$_1$ to C$_4$ alkylthio and/or halogen (preferably fluorine, chlorine, bromine or iodine, especially fluorine or chlorine), and furthermore represent an optionally C$_1$ to C$_6$ alkyl-substituted C$_5$ to C$_{10}$, especially C$_5$ or C$_6$, cycloalkyl radical, or represent an aralkyl radical which is optionally substituted in the aryl part by halogen (preferably fluorine, chlorine, bromine or iodine, especially fluorine or chlorine), nitro, C$_1$ to C$_6$ alkyl, cyano and/or trifluoromethyl, and which has 6 to 10 carbon atoms in the aryl part and 1 to 4 carbon atoms, preferably 1 or 2 carbon atoms, in the alkyl part, it being possible for the alkyl part to be straight-chain or branched, and represent C$_6$ to C$_{10}$ aryl which is optionally substituted by halogen (preferably fluorine, chlorine, bromine or iodine, especially fluorine or chlorine), nitro, cyano, C$_1$ to $C_6$, especially $C_1$ to $C_4$, alkyl, $C_1$ to $C_6$, especially $C_1$ to $C_4$, alkoxy, trifluoromethyl and/or dimethyldihydrofuranyl, $R^3$ additionally represents a hydrogen atom, and $R^4$ represents a trihalogenomethyl radical (preferably trichloromethyl or fluorodichloromethyl).

Very particularly preferred compounds according to the present invention are those in which $R^1$, $R^2$ and $R^3$ are identical or different and represent a $C_3$ to $C_5$ alkenyl or $C_3$ to $C_5$ alkinyl or $C_1$ to $C_6$ alkyl radical which is optionally substituted by methoxy, ethoxy, n-propyl, isopropoxy, methylthio, ethylthio, n-propylthio, isopropylthio, fluorine and/or chlorine, and furthermore represent a $C_5$ or $C_6$ cycloalkyl radical which is optionally substituted by methyl, ethyl, n-propyl, isopropyl, n-butyl, sec.-butyl, isobutyl or tert.-butyl, or represent an arylalkyl radical (preferably a benzyl or phenylethyl radical) which is optionally substituted in the aryl part by fluorine, chlorine, nitro, cyano, methyl, ethyl, n-propyl, i-propyl, n-butyl, sec.-butyl, isobutyl, tert.-butyl or trifluoromethyl, and further represents a $C_6$ to $C_{10}$ aryl radical (especially a phenyl or naphthyl radical) which is optionally substituted by fluorine, chlorine, nitro, methyl, ethyl, n-propyl, and isopropyl, n-butyl, isobutyl, sec.-butyl, tert.-butyl, methoxy, ethoxy, n-propoxy, isopropoxy, trifluoromethyl and/or dimethyldihydrofuranyl, and $R^3$ additionally represents a hydrogen atom, and $R^4$ represents a trichloromethyl or fluorodichloromethyl radical.

The radicals mentioned can be monosubstituted or polysubstituted by identical or different substituents.

In addition to the compounds of the formula (I) described in the preparative examples, the following compounds may be mentioned individually:

TABLE 1

$$R^1-N\begin{array}{c}COOR^2\\CO-NH-CO-N-SR^4\\|\\R^3\end{array} \quad (I)$$

| $R^1$ | $R^2$ | $R^3$ | $R^4$ |
|---|---|---|---|
| $CH_3$ | $CH_3$ | $CH_3$ | $CFCl_2$ |
| $CH_3$ | $C_2H_5$ | $CH_3$ | $CFCl_2$ |
| $CH_3$ | $i-C_3H_7$ | $CH_3$ | $CFCl_2$ |
| $CH_3$ | $n-C_3H_7$ | $CH_3$ | $CFCl_2$ |
| $CH_3$ | $i-C_4H_9$ | $CH_3$ | $CFCl_2$ |
| $CH_3$ | $t-C_4H_9$ | $CH_3$ | $CFCl_2$ |
| $C_2H_5$ | $C_2H_5$ | $C_2H_5$ | $CFCl_2$ |
| $C_2H_5$ | $i-C_3H_7$ | $C_2H_5$ | $CFCl_2$ |
| $C_2H_5$ | $t-C_4H_9$ | $C_2H_5$ | $CFCl_2$ |
| $i-C_3H_7$ | $i-C_3H_7$ | $i-C_3H_7$ | $CFCl_2$ |
| $t-C_4H_9$ | $CH_3$ | $CH_3$ | $CFCl_2$ |
| $t-C_4H_9$ | $C_2H_5$ | $CH_3$ | $CFCl_2$ |
| F—⟨phenyl⟩— | $C_2H_5$ | $CH_3$ | $CFCl_2$ |
| F—⟨phenyl⟩— | $C_2H_5$ | $CH_3$ | $CFCl_2$ |
| Cl,CF$_3$—⟨phenyl⟩— | $CH_3$ | $CH_3$ | $CFCl_2$ |
| Cl,F—⟨phenyl⟩— | $CH_3$ | $CH_3$ | $CFCl_2$ |
| Cl,CH$_3$—⟨phenyl⟩— | $CH_3$ | $CH_3$ | $CFCl_2$ |
| Cl—⟨phenyl⟩— | $CH_3$ | $CH_3$ | $CFCl_2$ |
| ⟨phenyl⟩— | $CH_3$ | $CH_3$ | $CFCl_2$ |
| $C_2H_5$ | 2,3-(CH$_3$)$_2$-⟨phenyl⟩— | $CH_3$ | $CFCl_2$ |
| $C_2H_5$ | 2,4,5-Cl$_3$-⟨phenyl⟩— | $CH_3$ | $CFCl_2$ |
| $C_2H_5$ | 2,4-Cl$_2$-⟨phenyl⟩— | $CH_3$ | $CFCl_2$ |
| $C_2H_5$ | 2-CH$_3$-⟨phenyl⟩— | $CH_3$ | $CFCl_2$ |
| $C_2H_5$ | 4-CH$_3$-⟨phenyl⟩— | $CH_3$ | $CFCl_2$ |

If, for example, N-methyl-N-phenoxycarbonyl-N-carbonyl isocyanate and N-ethyl-fluorodichloromethanesulphenamide are used as starting materials for the preparation of the compounds according to the invention, of the formula (I), the course of the reaction can be represented by the following equation:

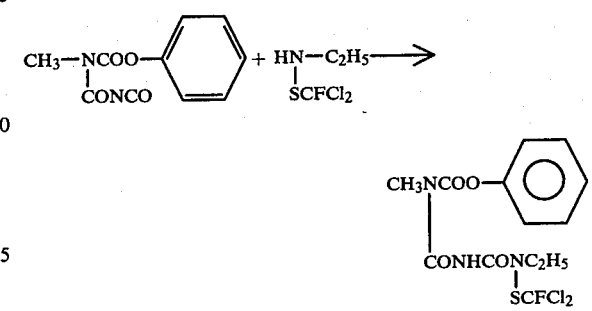

Preferred acyl isocyanates of formula (II) required as starting materials for the preparation of the compounds according to the present invention are those in which $R^1$ and $R^2$ have the meanings given for these radicals in the definition of the preferred, particularly preferred and very particularly preferred compounds according to the present invention.

The compounds of the formula (II) in which $R^1$ and $R^2$ represent alkyl are known and can be prepared according to processes which are known from the literature (Synthesis 1980, 112). In addition, the starting compounds of the formula (II) can be prepared according to a process which is not of the prior art, by reacting the N-substituted carbamic acid ester of the general formula

$$R^1-NH-COOR^2 \qquad (IV)$$

in which
$R^1$ and $R^2$ have the meanings given above,
with chlorocarbonyl isocyanate of the formula

$$Cl-CO-NCO \qquad (V)$$

in a diluent, at a temperature between 50° and 200° C. (see, also, the preparative examples hereinbelow).

The chlorocarbonyl isocyanate to be used, of the formula (V), is known, likewise the N-substituted carbamic acid esters of the formula (IV).

The starting compounds of the formula (III) which can be used according to the invention are known and can be prepared according to known processes (French Patent Specification 1,339,765 or Chem. Abstr. 60, 5519 (1964)). They are obtained when trihalogenomethanesulphenyl chloride is brought to reaction with a primary amine, for example in toluene as the solvent, in the temperature range between 0° and 30° C. (see, also, the preparative examples hereinbelow).

The reaction according to the invention is preferably carried out in the presence of a diluent. Any of the inert solvents such as hydrocarbons (for example toluene), chlorinated hydrocarbons (for example chlorobenzene) or ethers (for example dioxane), can be used as diluents.

The reaction temperatures can be varied within a relatively wide range. In general, the reaction is carried out at a temperature between 0° and 150° C., preferably between 20° and 120° C.

The reaction is preferably carried out under normal pressure.

In carrying out the reaction, the following procedure is preferred; the acyl isocyanate of the formula (II), dissolved in one of the diluents given, is initially introduced, and the sulphenamide of the formula (III) is added dropwise at room temperature. During the procedure, the temperature of the reaction mixture increases. The reaction solution is freed of the diluent by distillation in vacuo. The residue can be recrystallized from an organic solvent.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Pyricularia oryzae, the blast disease causative organism, and for combating Leptosphaeria nodorum in wheat, and Xanthomonas oryzae in rice. In addition, the compounds have an action against Phytophthora and against Botrytis.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic metals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are generally required at the place of action.

The present invention also provides a microbicidal composition containing as active ingredient a compound of the present invention in admixture with a solid or liquefied gaseous diluent or carrier or in admixture with a liquid diluent or carrier containing a surface-active agent.

The present invention also provides a method of combating microbes, especially fungi or bacteria, which comprises applying to the microbes, or to a habitat thereof, a compound of the present invention alone or in the form of a composition containing as active ingredient a compound of the present invention in admixture with a diluent or carrier.

The present invention further provides crops protected from damage by microbes by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is illustrated in the following example:

EXAMPLE I (a) Preparation of the starting materials of the formula (II)

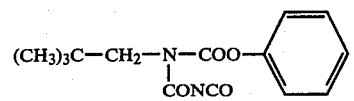

62 g (0.3 mol) of O-phenyl N-neopentylcarbamate were dissolved in 200 ml of dry chlorobenzene, and the solution was added dropwise to a solution of 35 g (0.33 mol) of chlorocarbonyl isocyanate in 70 ml of dry chlorobenzene. No noticeable reaction took place at room temperature. When the reaction solution was heated, hydrogen chloride was evolved continuously at about 95° C. and above. After about 1.5 to 2 hours, when the boiling point of the chlorobenzene was reached, this evolution of gas ceased. The solvent was distilled off in vacuo. The residue gave 68 g (88% of theory) of O-phenyl N-neopentyl-N-carbonylisocyanato-carbamate of boiling point 111° to 112° C./0.1 mm Hg by distillation under a high vacuum.

The following products of the formula

TABLE 2

$$R^1-N-COOR^2 \atop | \atop CONCO \qquad II$$

| $R^1$ | $R^2$ | Boiling point (°C./mm Hg) |
|---|---|---|
| $CH_3-$ | $C_6H_5-$ | 97/0.08 |
| $i-C_3H_7$ | $C_6H_5-$ | 125/0.1 |
| $i-C_4H_9-$ | $C_6H_5-$ | 95–96/0.09 |
| ⟨H⟩ (cyclopentyl) | $C_6H_5-$ | 128–130/0.08 |
| ⟨H⟩ (cyclohexyl) | $C_6H_5-$ | 145–150/0.1 |
| phenyl | $C_6H_5-$ | 162/0.1 |
| $CH_3-$ | 2-isopropoxyphenyl (i-OC$_3$H$_7$) | 132–133/0.1 |
| $CH_3-$ | 2,2-dimethylbenzofuran-type (CH$_3$, CH$_3$, O) | 152/0.1 |
| phenyl | $C_2H_5$ | 130–135/0.8 |

TABLE 2-continued

| $R^1$ | $R^2$ | Boiling point (°C./mm Hg) |
|---|---|---|
| $(CH_3)_3C-CH_2-$ | $C_2H_5$ | 70–74/0.2 |

(b) Preparation of the precursors of the formula (III)

$$FCl_2C-S-NH-C(CH_3)_3$$

73 g (1 mol) of tert.-butylamine were dissolved in 300 ml of toluene, and 85 g (0.5 mol) of fluorodichloromethane-sulphenyl chloride were added dropwise at 20° to 30° C., while cooling. The toluene solution was extracted by shaking with water, dried over sodium sulphate and concentrated in vacuo, and the residue was distilled 80 g (77% of theory) of fluorodichloromethane-sulphenyl-N-(t-butyl)-amide of boiling point 60° to 65° C./13 mm Hg were obtained.

(c)

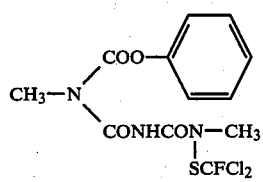

14 g (0.063 mol) of O-phenyl-N-methyl-N-(isocyanatocarbonyl)-carbamate were dissolved in 50 ml of dioxane, and 105 g (0.07 mol) of fluorodichloromethane-sulphenyl-N-methylamide were added dropwise at room temperature. During this procedure, the temperature increased to 60° C. The reaction solution was concentrated in vacuo, and the residue was recrystallized from methanol. 18 g (78% of theory) of N''-methyl-N''-phenoxycarbonyl-N-methyl-N-fluorodichloromethylthio-biuret of melting point 119°–120° C. were obtained.

The compounds of the formula

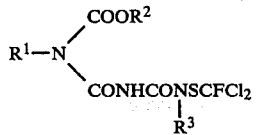

which are listed in the table below were obtained in an analogous manner:

TABLE 3

| Compound No. | $R^1$ | $R^2$ | $R^3$ | Melting point (°C.); refractive index ($n_D^{20}$) |
|---|---|---|---|---|
| 2 | $CH_3$ | $C_6H_5$ | $C_2H_5$ | 85–89 |
| 3 | " | " | n-$C_3H_7$ | 130–132 |
| 4 | " | " | tert.-$C_4H_9$ | 132 |
| 5 | " | " | $C_6H_{11}$ | 136 |
| 6 | i-$C_3H_7$ | $CH_3$ | $CH_3$ | 1.4989 |
| 7 | " | " | $C_2H_5$ | 1.5009 |
| 8 | " | " | tert.-$C_4H_9$ | 1.4907 |
| 9 | " | " | i-$C_3H_7$ | 1.5051 |
| 10 | i-$C_3H_7$ | $C_6H_5$ | $CH_3$ | 1.5271 |
| 11 | " | " | n-$C_3H_7$ | 1.5187 |
| 12 | $(CH_3)_3C-CH_2$ | " | $CH_3$ | 100–105 |
| 13 | " | " | $C_2H_5$ | 1.5230 |
| 14 | " | " | n-$C_3H_7$ | 1.5212 |
| 15 | " | " | i-$C_3H_7$ | 1.5364 |
| 16 | " | " | n-$C_4H_9$ | 1.5153 |
| 17 | " | " | tert.-$C_4H_9$ | 1.5184 |
| 18 | " | " | $C_6H_{11}$ | 1.5307 |
| 19 | " | " | $C_6H_5$ | 1.5549 |
| 20 | $(CH_3)_3C-CH_2$ | $CH_3$ | i-$C_3H_7$ | 1.4918 |
| 21 | $(CH_3)_3C-CH_2$ | $CH_3$ | $C_6H_{11}$ | 1.5072 |
| 22 | " | " | tert.-$C_4H_9$ | 1.4894 |
| 23 | " | " | i-$C_6H_9$ | 1.4728 |
| 24 | $C_6H_{11}$ | $C_6H_5$ | i-$C_3H_7$ | wax-like |
| 25 | $C_6H_5$ | " | $CH_3$ | 88 |
| 26 | " | " | H | 142–145 |
| 27 | " | " | tert.-$C_4H_9$ | 131–135 |
| 28 | " | " | $C_6H_{11}$ | 128–131 |
| 29 | " | $C_2H_5$ | $C_2H_5$ | 1.5049 |
| 30 | " | " | $CH_3$ | 1.5409 |
| 31 | " | " | tert.-$C_4H_9$ | 1.5234 |
| 32 | $C_6H_5$ | $C_2H_5$ | $C_6H_{11}$ | 1.5263 |
| 33 | " | $C_6H_5$ | $C_2H_5$ | 88 |
| 34 | i-$C_3H_7$ | $CH_3$ | n-$C_3H_7$ | wax-like |
| 35 | $(CH_3)_3C-CH_2$ | $C_6H_5$ | H | yellow oil |

The fungicidal or bactericidal activity of the compounds of this invention is illustrated by the following biotest examples.

In these examples, the compounds according to the present invention are each identified by the number (given in brackets) from Example 1 and Table 3.

The known comparison compounds are identified as follows:

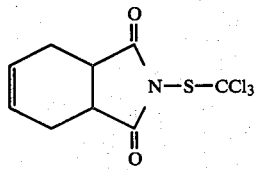

(A)

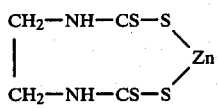

(B)

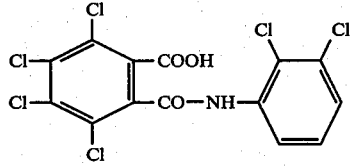

(C)

EXAMPLE 2

*Leptosphaeria nodorum* test (wheat)/protective

Solvent: 100 parts by weight of dimethylformamide
Emulsifier: 0.25 part by weight of alkylaryl polyglycol ether To produce a suitable preparation of active compound, 1 part by weight of active compund was mixed with the stated amounts of solvent and emulsifier, and the concentrated was diluted with water to the desired concentration.

To test for protective activity, young plants were sprayed with the preparation of active compound until dew-moist. After the spray coating had dried on, the plants were sprayed with a conidia suspension of *Leptosphaeria nodorum*. The plants remained for 48 hours in an incubation cabinet at 20° C. and 100% relative atmospheric humidity.

The plants were placed in a greenhouse at a temperature of about 15° C. and a relative atmospheric humidity of about 80%.

Evaluation was effected 10 days after the inoculation.

In this test, a clearly superior activity compared with the compound A known from the prior art was shown, for example, by the compounds: (1), (6), (20), (22), (33), (2), (3), (10), (11) and (9).

EXAMPLE 3

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound was mixed with the stated amount of solvent, and the concentrate was diluted with water and the stated amount of emulsifier, to the desired concentration.

To test for protective activity, young rice plants were sprayed with the preparation of active compound until dripping wet. After the spray coating had dried off, the plants were inoculated with an aqueous spore suspension of *Pyricularia oryzae*. The plants were then placed in a greenhouse at 100% relative atmospheric humidity and 25° C.

Evaluation of the disease infestation was carried out 4 days after the inoculation.

In this test, a clearly superior activity compared with the compound B known from the prior art was shown, for example, by the compounds: (12), (25), (13), (7), (8), (34) and (33).

EXAMPLE 4

*Xanthomonas oryzae* test/bacteriosis/rice/protective
Solvent: 24.25 parts by weight of acetone
Emulsifier: 0.75 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous suspension of *Xanthomonas oryzae* by pricking the leaves. After the incubation period of 48 hours at 100% relative atmospheric humidity, the plants remained in a greenhouse for 10 days at 24° to 26° C. and 70 to 80% relative atmospheric humidity until they were evaluated.

In this test, a clearly superior activity compared with the compound C known from the prior art was shown, for example, by the compounds: (35), (12), (13) and (14).

It will be appreciated that the instant specification and examples are set forth by way of illustration and not limitation, and that various modifications and changes may be made without departing from the spirit and scope of the present invention.

We claim:

1. An N-sulphenylated biuret-N"-carboxylic acid ester of the formula

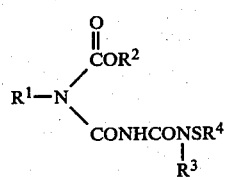

in which
$R^1$, $R^2$ and $R^3$ each independently is a $C_2$ to $C_{10}$ alkenyl or $C_2$ to $C_{10}$ alkinyl or $C_1$ to $C_{10}$ alkyl radical which is optionally substituted by $C_1$ to $C_4$ alkoxy, $C_1$ to $C_4$ alkylthio and/or halogen, an optionally $C_1$ to $C_6$ alkyl-substituted $C_5$ to $C_{10}$ cycloalkyl radical, an aralkyl radical which is optionally substituted in the aryl part by halogen, nitro, $C_1$ to $C_6$ alkyl, cyano and/or trifluoromethyl, and which has 6 to 10 carbon atoms in the aryl part and 1 to 4 carbon atoms in the alkyl part, or $C_6$ to $C_{10}$ aryl which is optionally substituted by halogen, nitro, cyano, $C_1$ to $C_6$ alkyl, $C_1$ to $C_6$ alkoxy, trifluoromethyl and/or dimethyldihydrofuranyl,
and $R^3$ additionally may be a hydrogen atom,
and $R^4$ is a trihalogenomethyl radical.

2. A compound according to claim 1, in which
$R^1$, $R^2$ and $R^3$ each independently is a $C_3$ to $C_5$ alkenyl or $C_3$ to $C_5$ alkinyl or $C_1$ to $C_6$ alkyl radical which is optionally substituted by methoxy, ethoxy, n-propyl, isopropoxy, methylthio, ethylthio, n-propylthio, isopropylthio, fluorine and/or chlorine, a $C_5$ or $C_6$ cycloalkyl radical which is optionally substituted by methyl, ethyl, n-propyl, isopropyl, n-butyl, sec.-butyl, isobutyl or tert.-butyl, a benzyl or phenylethyl radical which is optionally substituted in the aryl part by fluorine, chlorine, nitro, cyano, methyl, ethyl, n-propyl, i-propyl, n-butyl, sec.-butyl, isobutyl, tert.-butyl or trifluoromethyl, or a phenyl or naphthyl radical which is optionally substituted by fluorine, chlorine, nitro, methyl, ethyl, n-propyl, isopropyl, n-butyl, isobutyl, sec.-butyl, tert.-butyl, methoxy, ethoxy, n-propoxy, isopropoxy, trifluoromethyl and/or dimethyldihydrofuranyl, and
$R^3$ additionally may be a hydrogen atom, and
$R^4$ is a trichloromethyl or fluorodichloromethyl radical.

3. A compound according to claim 1, wherein such compound is N"-methyl-N"-phenoxycarbonyl-N-methyl-N-fluorodichloromethylthio-biuret of the formula

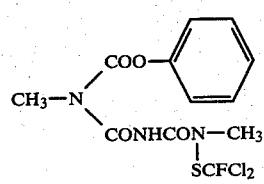

4. A compound according to claim 1, wherein such compound is N"-isopropyl-N"-methoxycarbonyl-N-methyl-N-fluorodichloromethylthio-biuret of the formula

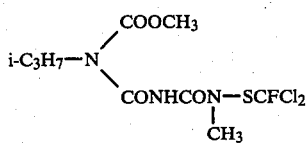

5. A compound according to claim 1, wherein such compound is N''-neopentyl-N''-phenoxycarbonyl-N-methyl-N-fluorodichloromethylthio-biuret of the formula

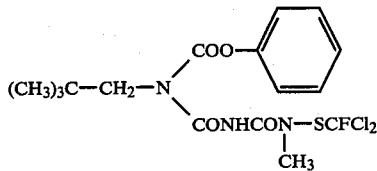

6. A compound according to claim 1, wherein such compound is N''-neopentyl-N''-phenoxycarbonyl-N-ethyl-N-fluorodichloromethylthio-biuret of the formula

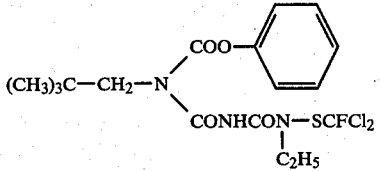

7. A compound according to claim 1, wherein such compound is N''-phenyl-N''-phenoxycarbonyl-N-ethyl-N-fluorodichloromethylthio-biuret of the formula 8. A fungicidal and bactericidal composition, comprising a fungicidally and bactericidally amount of a compound according to claim 1 in admixture with a diluent.

9. A method of combating fungi and bacteria comprising applying to the fungi, bacteria, or to a habitat thereof, a fungicidally and bactericidally effective amount of a compound according to claim 1.

10. The method according to claim 9, wherein such compound is
N''-methyl-N''-phenoxycarbonyl-N-methyl-N-fluorodichloromethylthio-biuret,
N''-isopropyl-N''-methoxycarbonyl-N-methyl-N-fluorodichloromethylthio-biuret,
N''-neopentyl-N''-phenoxycarbonyl-N-methyl-N-fluorodichloromethylthio-biuret,
N''-neopentyl-N''-phenoxycarbonyl-N-ethyl-N-fluorodichloromethylthio-biuret, or
N''-phenyl-N''-phenoxycarbonyl-N-ethyl-N-fluorodichloromethylthio-biuret.

* * * * *